(12) United States Patent
Uchiyama

(10) Patent No.: US 8,790,384 B2
(45) Date of Patent: Jul. 29, 2014

(54) SKIN PATCH LAMINATE BODY

(75) Inventor: Hitoshi Uchiyama, Ibaraki-ken (JP)

(73) Assignee: Okamoto Industries, Inc., Tokyo (JP)

( * ) Notice: Subject to any disclaimer, the term of this patent is extended or adjusted under 35 U.S.C. 154(b) by 204 days.

(21) Appl. No.: 13/038,041

(22) Filed: Mar. 1, 2011

(65) Prior Publication Data
US 2011/0218601 A1  Sep. 8, 2011

(30) Foreign Application Priority Data
Mar. 5, 2010  (JP) .................................. 2010-049590

(51) Int. Cl.
*A61F 7/03*  (2006.01)
*A61F 7/02*  (2006.01)
*A61F 7/00*  (2006.01)

(52) U.S. Cl.
CPC . *A61F 7/03* (2013.01); *A61F 7/032* (2013.01); *A61F 7/034* (2013.01); *A61F 2007/003* (2013.01); *A61F 2007/0032* (2013.01); *A61F 2007/0034* (2013.01); *A61F 2007/0226* (2013.01)
USPC ........................................................ 607/112

(58) Field of Classification Search
CPC ........... A61F 7/03; A61F 7/032; A61F 7/034; A61F 2007/003; A61F 2007/0032; A61F 2007/0034; A61F 2007/0226
USPC ........................................................ 607/112
See application file for complete search history.

(56) References Cited

U.S. PATENT DOCUMENTS

| | | | |
|---|---|---|---|
| 5,300,103 A * | 4/1994 | Stempel et al. | 607/108 |
| 5,534,021 A * | 7/1996 | Dvoretzky et al. | 607/112 |
| 5,887,437 A * | 3/1999 | Maxim | 62/4 |
| 6,245,347 B1 * | 6/2001 | Zhang et al. | 424/449 |
| 6,261,595 B1 | 7/2001 | Stanley et al. | |
| 6,306,431 B1 | 10/2001 | Zhang et al. | |
| 6,599,262 B1 * | 7/2003 | Masini | 602/2 |
| 6,726,673 B1 * | 4/2004 | Zhang et al. | 604/500 |

(Continued)

FOREIGN PATENT DOCUMENTS

| | | |
|---|---|---|
| CA | 2 228 137 C | 1/2005 |
| CN | 1543342 A | 11/2004 |

(Continued)

OTHER PUBLICATIONS

Extended European Search Report in the counterpart European Patent Application No. 11 15 6576.8, issued on Nov. 9, 2011 (4 pages).

(Continued)

*Primary Examiner* — Linda Dvorak
*Assistant Examiner* — Kaitlyn Smith
(74) *Attorney, Agent, or Firm* — Fitch, Even, Tabin & Flannery, LLP

(57) ABSTRACT

The present invention provides a skin patch laminate body, comprising a skin patch body including a base layer and a skin adhesive layer being formed on one surface of the base layer for being directly applied to the skin and a heat imparting body including an exothermic agent and an exothermic agent-accommodating layer that accommodates the exothermic agent therein, wherein the exothermic agent-accommodating layer on one surface of the heat imparting body, and the other surface of the base layer of the skin patch body are attached to each other via a peelable adhesive layer.

18 Claims, 2 Drawing Sheets

(56) References Cited

U.S. PATENT DOCUMENTS

| | | | |
|---|---|---|---|
| 6,756,053 B2 | 6/2004 | Zhang et al. | |
| 7,264,602 B1* | 9/2007 | Longsworth | 602/2 |
| 7,614,399 B2* | 11/2009 | Carstens | 128/206.21 |
| 7,621,110 B2* | 11/2009 | Ota et al. | 53/477 |
| 7,767,936 B2* | 8/2010 | Ferguson | 219/219 |
| 8,123,791 B2* | 2/2012 | Nakamura | 607/108 |
| 8,261,734 B2* | 9/2012 | Dodo | 126/204 |
| 8,445,819 B2* | 5/2013 | Ferguson | 219/219 |
| 2002/0119186 A1* | 8/2002 | Zhang et al. | 424/449 |
| 2005/0196562 A1* | 9/2005 | Ota et al. | 428/34.1 |
| 2006/0173519 A1* | 8/2006 | Matsuo et al. | 607/108 |
| 2006/0210752 A1* | 9/2006 | Ota et al. | 428/40.1 |
| 2007/0101996 A1* | 5/2007 | Carstens | 128/206.12 |
| 2007/0102461 A1* | 5/2007 | Carstens | 224/222 |
| 2007/0106350 A1* | 5/2007 | Carstens | 607/108 |
| 2007/0108190 A1* | 5/2007 | Ferguson | 219/545 |
| 2009/0188614 A1* | 7/2009 | Ota et al. | 156/256 |
| 2010/0087902 A1* | 4/2010 | Ota et al. | 607/112 |
| 2010/0198325 A1* | 8/2010 | Ishikawa | 607/112 |

FOREIGN PATENT DOCUMENTS

| | | |
|---|---|---|
| CN | 1899644 A | 1/2007 |
| JP | H10-201787 A | 8/1998 |
| JP | 2006-026370 A | 2/2006 |
| JP | 2008-200450 A | 9/2008 |
| WO | 97/04728 A1 | 2/1997 |

OTHER PUBLICATIONS

Office Action issued in counterpart Chinese Application No. 201110060975.X, dated Dec. 24, 2013 and English translation of the same (14 pages).

* cited by examiner

SKIN PATCH LAMINATE BODY

RELATED APPLICATIONS

This application claims priority under 35 U.S.C. §119 to Japanese Patent Application No. JP2010-049590 filed on Mar. 5, 2010, the entire content of which is hereby incorporated herein by reference in its entirety.

FIELD OF THE INVENTION

The present invention relates to a laminate body that is applied to the skin, which comprises an exothermic body.

BACKGROUND OF THE INVENTION

Conventionally, when a transdermal analgesic anti-inflammatory adhesive plaster is hyperthermically applied to the skin of an affected area, a configuration has been suggested, in which a disposable heating pad is previously attached to the back side of the drug application surface of an adhesive plaster. In addition, a configuration has been suggested in which protrusions that stimulate pressure points are added to a disposable heating pad for foot, wherein a magnet is used as the protrusion, which is aimed to give effects of improving the symptom of excessive sensitivity to cold as well as warming effects of the disposable heating pad for foot. Furthermore, a configuration has been suggested of a skin patch that is integrated with a disposable heating pad, which is characterized by setting up an adhesive layer on the front or back surface of a bag of a disposable heating pad, wherein the bag of a disposable heating pad is formed by inclusion of an exothermic material therein, further flattening a medicated salve of a Chinese herbal medicine and the like to a sheet, and attaching a release sheet to the surface of the medicated salve to form a skin patch, and attaching the sheet of the skin patch to the adhesive layer of the disposable heating pad, which is intended to attempt synergy effects of warming by the heating pad and hyperthermic stimulation by the skin patch. Furthermore, for a medicated salve that is usable for a long time, it is disclosed that the skin patch is peeled off from the disposable heating pad when exothermic effects of the disposable heating pad disappear, and a new disposable heating pad is attached to the skin patch, whereby to reuse the skin patch.

SUMMARY OF THE INVENTION

The object of the present invention is to provide a skin patch laminate body that has a heat imparting body comprising an exothermic agent, and a skin patch body comprising a portion that functions by being applied to the skin, which makes it possible to conveniently peel off only the heat imparting body after the heat imparting body completes heat generation.

According to one viewpoint of the present invention, provided is a skin patch laminate body that has a skin patch body having a base layer and a skin adhesive layer being formed on one surface of this base layer for being directly applied to the skin; and a heat imparting body having an exothermic agent and an exothermic agent-accommodating layer that accommodates this exothermic agent, which is characterized that the exothermic agent-accommodating layer on one surface of the above-mentioned heat imparting body, and the other surface of the above-mentioned base layer of the above-mentioned skin patch body are formed to be attached via a peelable adhesive layer.

In one form, an exothermic skin patch laminate body is provided including a skin patch body including a base layer having opposite surfaces and a skin adhesive layer on one of the opposite surfaces of the base layer for being directly applied to the skin; and a heat imparting body including an exothermic agent and an exothermic agent-accommodating layer that accommodates the exothermic agent therein, wherein the exothermic agent-accommodating layer of the heat imparting body, and the other of the opposite surfaces of the base layer of the skin patch body are attached to each other via a peelable adhesive layer so that the peelable adhesive layer, the heat imparting body, and the skin patch body are integrated into the exothermic skin patch laminate body with the peelable adhesive layer releasably adhering the heat imparting body and the skin patch body together to allow a user to apply the skin patch body to the skin with the heat imparting body already releasably adhered to skin patch body without requiring the user to separately apply the heat imparting body onto the skin patch body and to further allow the user to peel off the heat imparting body from the skin patch body after the heat imparting body completes heat generation while the skin patch body remains applied to the skin.

In another form, the skin patch body has an outermost perimeter and the heat imparting body has an outermost perimeter with the outermost perimeters of the skin patch body and the heat imparting body being of substantially the same size and configuration such that with the skin patch body and the heat imparting body releasably adhered together no perimeter portions of either one of the bodies projects beyond the other body.

In another form, the heat imparting body is entirely above the skin patch body so that only the skin adhesive layer of the skin patch body is used to adhere the exothermic skin patch laminate body to the skin.

In another form, the skin patch body and the heat imparting body have substantially identical elongate configurations including opposite longitudinal ends with neither one of the bodies extending beyond the other body, and the peelable adhesive layer is spaced from at least one of the opposite longitudinal ends of each of the bodies that are adjacent to each other to allow for the heat imparting body to be readily peeled off from the skin patch body in a longitudinal direction at the one longitudinal end thereof.

In another form, the peelable adhesive layer tapers down to a narrow end portion spaced from the one of the longitudinal ends of each of the bodies that are adjacent to each other.

In another form, the peelable adhesive layer has gaps therein for travel of air therethrough and through the breathable exothermic agent-accommodating layer that the peelable adhesive layer releasably adheres to the other surface of the base layer for supplying air to the exothermic agent.

In another form, the exothermic skin patch laminate body is provided in combination with a sealed bag wherein both the skin patch body and the heat imparting body releasably adhered together via the peelable adhesive layer to be integrated into the exothermic skin patch laminate body are contained in the sealed bag so that when the sealed bag is opened both the skin patch body and the heat imparting body are simultaneously exposed to air.

In another form, the skin adhesive layer includes an adhesive composition and the peelable adhesive layer includes an adhesive agent that has an adhesive strength that is less than that of the adhesive composition of the skin adhesive layer to allow for only the heat imparting body to be peeled off from the skin patch body while the skin patch body remains applied to the skin.

DETAILED DESCRIPTION OF THE PREFERRED EMBODIMENTS

The skin patch laminate body in each embodiment of the present invention will be explained below with reference to the drawings.

First Embodiment

Figure 1:
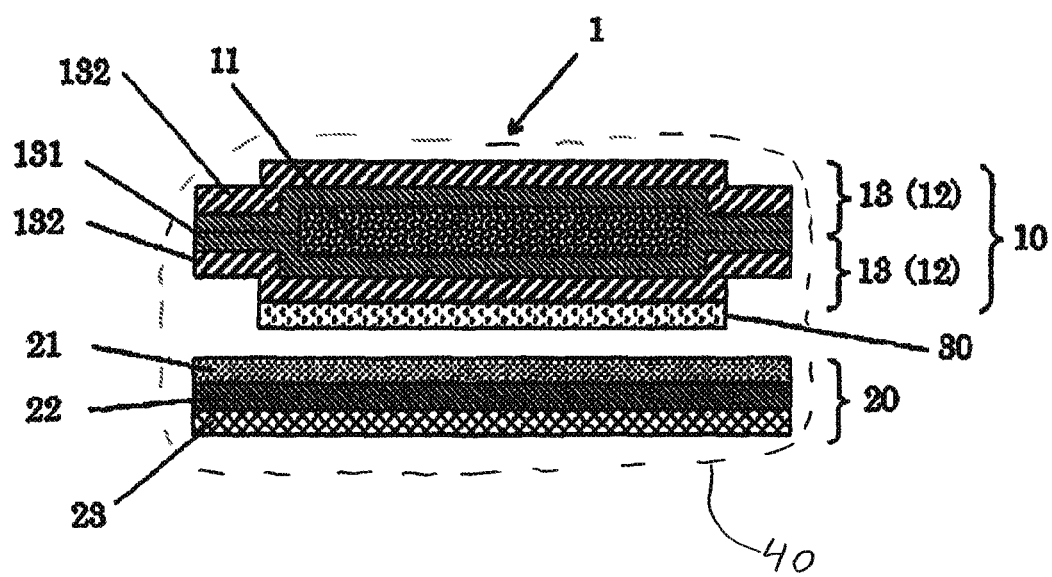
FIG. 1 is a sectional view of a skin patch laminate body, which is Example 1 of the present invention.

FIG. 1 is a sectional view that shows the skin patch laminate body according to the first embodiment. As shown in FIG. 1, the skin patch laminate body 1 includes a heat imparting body 10, a skin patch body 20, and a peelable adhesive layer 30.

The heat imparting body 10 is formed such that two exothermic agent-accommodating layers 12 accommodate an exothermic agent 11 in a flat form from the both sides. According to this embodiment, each of the exothermic agent-accommodating layers 12 is formed as a breathable layer 13 for exposing the exothermic agent 11 to air to generate heat oxidatively. By both surfaces of the heat imparting body being rendered to have air permeability, it is possible to send more air to the exothermic agent, whereby to render the exothermic agent to be rapidly hyperthermic. However, the other surface (the surface of the peelable layer) side needs to be formed so as to supply air to the exothermic agent when forming the peelable adhesive agent layer (detailed description will be described below).

The skin patch body 20 has a base layer 21, a skin adhesive layer 22 and a release sheet 23. The base layer 21 functions as a base layer of the skin patch body 20. The skin adhesive layer 22 has a medicine containing an active ingredient, or a solid material or the like for treatment and functions by being applied to the skin, which is on the undersurface of the base layer 21. Furthermore, the release sheet 23 is peelable from the skin adhesive layer 22, which is on the undersurface of the skin adhesive layer 22.

The peelable adhesive layer 30 is located between the base layer 21 of the skin patch body 20 and one of the breathable layer 13 of the heat imparting body 10, and attaches the skin patch body 20 to the heat imparting body 10. In this manner, the heat imparting body 10, the skin patch body 20, and the peelable adhesive layer 30 are integrated to form the skin patch laminate body 1.

A user of the skin patch laminate body 1 takes out the skin patch laminate body 1, which is normally sealed and packed in a bag 40 to prevent the exothermic agent 11 from generating heat oxidatively, from the bag 40 in use, peels off the release sheet 23 from the skin patch laminate body 1, and applies the skin patch laminate body 1 to the skin of an affected area of the user. The exothermic agent 11 begins to be exothermic from a time point when the bag 40 is ripped off and the exothermic agent 11 is exposed to oxygen, and the thermal effects may be exerted rapidly by increasing the number of ventilation pores (not shown) of the breathable layer 13 whereby to expedite the speed of exposure to oxygen, or by reducing the moisture amount contained in the exothermic agent 11. As a result, the user will not feel cold since the skin patch laminate body 1 is warmed already when applied to the skin, and feel warmed immediately.

However, exothermic effects of the heat imparting body 10 last for several hours whereas the efficacy of the skin adhesive layer 22 lasts normally longer than duration of the exothermic effects of the heat imparting body. Therefore, when the exothermic effects of the heat imparting body 10 disappear, it may be troublesome to the user to have the heat imparting body 10 as applied to the skin, which is normally thicker than the skin patch body 20. Therefore, since the heat imparting body 10 and the skin patch body 20 are attached to each other by the peelable adhesive layer 30 with easy peeling property, the user can easily peel off only the heat imparting body 10 while retaining the skin patch body 20 as applied to the skin, whereby to retain the skin patch body 20 still having efficacy as applied.

The skin patch laminate body will be further explained in detail below. The skin patch laminate body 1 adopts a disposable heating pad as the heat imparting body 10, and adopts a plaster, which has adhesive property and uses a percutaneous absorption agent and the like as a medicine, as the skin adhesive layer 22.

In the heat imparting body 10 of the disposable heating pad, the breathable layer 13, which includes an air-permeable porous film 131 and a nonwoven cloth 132, encapsulates the exothermic agent 11 from the both sides. The exothermic agent 11 is a powder mixture obtained by mixing, for example, iron powder, water, vermiculite, activated carbon, salts and the like, and becomes exothermic by reaction to oxygen. As the exothermic agent, those obtained by molding the powder mixture into a sheet shape, or those obtained by rendering a sheet-shape product to hold the powder mixture therein may be used. The porous film 131 of the breathable layer 13 is punched to have multiple ventilation pores (not shown). As a matter of course, the porous film 131 is not limited thereto, and may have air permeability at least partially so as to supply oxygen to the internal exothermic agent 11. In addition, needless to say, the nonwoven cloth 132 of the breathable layer 13 has air permeability essentially. The reason for inclusion of the nonwoven cloth 132 in the ventilation layer 13 is to give good touch feeling to the user, thereby enhancing use feeling. However, materials such as other woven cloths and the like may be also used if they have air permeability.

The skin patch body 20 is a plaster that has the base layer 21 and the skin adhesive layer 22. The base layer 21 is made of a flexible material such as a woven cloth or nonwoven cloth, or a polymer compound such as polyurethane and the like. The skin adhesive layer 22 is made of an adhesive composition comprising an active ingredient such as a percutaneous analgesic agent and a fomentations agent, and which is on the undersurface of the base layer 21. The skin adhesive layer 22 may be anything that forms a skin patch such as a transdermal analgesic anti-inflammatory adhesive plaster, a Chinese herbal medicine skin patch, a healing ointment, a fomentation, undo blood circulation promotion agent, and is used as applied to the skin to cure roughly shoulder discomfort, low back pain, muscle pain and the like. In addition, this skin adhesive layer 22 may comprise a skin care medicine of which original effects are enhanced by thermal effects. For example, in a case of a hair removal cream, the pores open by thermal effects, whereby to perform hair removal more effectively.

The peelable adhesive layer 30 attaches the nonwoven cloth 132, which is one of the breathable layer 13 of the heat imparting body 10 of the disposable heating pad, to the base layer 21 of the skin patch body 20 of the plaster. When an acrylic adhesive agent or the like is used as this peelable adhesive layer 30, the adhesive strength between the nonwoven cloth 132 and the base layer 21 is influenced by the heat of the heat imparting body 10 of the disposable heating pad, or a temporal element. As a result, it is difficult to control the adhesive strength such that the heat imparting body 10 of the disposable heating pad is not peeled and dropped off carelessly, and only the heat imparting body 10 is peeled off when it becomes unnecessary. On the other hand, if the nonwoven cloth 132 and the base layer 21 are attached to each other using an adhesive agent having easy peeling property, the adhesive strength is stable, which allows no consideration on the heat influence or temporal change.

As the adhesive agent having easy peeling property, for example, a peelable agent made of a soluble nitrocellulose (nitrocellulose) resin, a polyamide resin, a polyester resin, a urethane resin or the like may be used, but the adhesive agent is not limited thereto. According to this embodiment, such peelable agent is first administered to the nonwoven cloth 132, which is the breathable layer 13 of the heat imparting body 10, and then is attached to the skin patch body 20, whereby to form the skin patch laminate body 1. However, the present invention is not limited thereto. In addition, the peelable adhesive layer 30 may be formed by a print type such as gravure print type, offset print type, screen print type and letter press print type using a peelable coating agent. According to this configuration, the peelable adhesive layer 30 can be formed to various patterns easily (detailed description will be described below).

The relationship between the adhesive strength to the skin of the skin adhesive layer 22 of the skin patch body 20, which is a plaster having adhesive property using a percutaneous absorption agent and the like as a medicine and the adhesive strength and the easy peeling property of the peelable adhesive layer 30 will be accomplished as described below.

First, the peelable adhesive layer 30 needs to have at least 0.2 Newton/25 mm or so of the adhesive strength in a peeling test for the peelable adhesive layer 30 so as not to be dropped off carelessly in use or the like. On the other hand, from a view of easy peeling property, the adhesive strength of the peelable adhesive layer 30 needs to be less than the adhesive strength to the skin of the skin adhesive layer 22 of the skin patch body 20. In an opposite case, when the heat imparting body 10 of the disposable heating pad is peeled off, the skin patch body 20 will be peeled off together. According to the experiments of the inventors, the difference of the adhesive strength of the peelable adhesive layer 30, and the adhesive strength to the skin of the skin adhesive layer 22 needs to be about 0.8 Newton/25 mm so as to allow easy peeling off of only the heat imparting body 10 of the disposable heating pad. Consequently, the adhesive strength to the skin of the skin adhesive layer 22 is at least about 1.0 Newton/25 mm.

It is preferable that the adhesive strength of the peelable adhesive layer 30 is more than 0.2 Newton/25 mm, and if the difference of the adhesive strength of the peelable adhesive layer 30 and the adhesive strength to the skin of the skin adhesive layer 22 is bigger, the heat imparting body 10 of the disposable heating pad is less likely to be peeled and dropped off, and the difference of the adhesive strength becomes broad, which make it possible to more easily peel off the heat imparting body 10 of the disposable heating pad. For example, when the adhesive strength to the skin of the skin adhesive layer 22 is about 1.7 Newton/25 mm, the adhesive strength of the peelable adhesive layer 30 may become about 0.3 Newton/25 mm. In addition, when the adhesive strength to the skin of the skin adhesive layer 22 is about 3.0 Newton/25 mm, the adhesive strength of the peelable adhesive layer 30 may become about 0.4 Newton/25 mm.

With regard to such peelable adhesive strength of the peelable adhesive layer 30, easy peeling property may be adjusted by mixing waxes with the peelable agent described above, or adjusted by changing the surface area or the shape of the adherend of the peelable adhesive layer 30 (detailed description will be described below).

The conventional disposable heating pad, in which a drug application surface and a disposable heating pad are attached to each other, or a raised body on the heating pad is created, has no configuration of separating a disposable heating pad and another portion for therapeutic action. Therefore, when exothermic effects of the disposable heating pad disappear, the other portion for therapeutic action has to be disposed in addition to the disposable heating pad.

In addition, according to the conventional disposable heating pad, when exothermic effects of the disposable heating pad disappear, the skin patch is peeled off from the disposable heating pad, and a new disposable heating pad is attached to the skin patch, whereby to reuse the skin patch. However, it was impossible to peel off only the disposable heating pad and not peel off the sheet that flattens the medicated salve from the skin, and it was necessary to peel off the sheet from the skin before peeling off the heating pad from the sheet. However, since a second or later patch becomes weak in adhesive strength of the sheet and becomes easily peeled off, the problem was how to conveniently peel off only the exothermic body that is a disposable heating pad, and retain the other portion for therapeutic action on the skin.

According to this embodiment, it is possible to peel off the heat imparting body that comprises the skin adhesive layer that functions by being applied to the skin, while retaining the skin patch body being as applied to the skin, after exothermic effects of the heat imparting body disappear. According to this configuration, it is possible to easily adjust the adhesive strength and to form a peelable adhesive layer so as to be flexible.

According to this embodiment, it is possible to provide a skin patch laminate body that accommodates an exothermic agent with air permeability maintained, and feels soft. Furthermore, it is possible to provide a skin patch laminate body which allows the release sheet to be peeled off from the skin adhesive layer when applied to the skin, and which is easy to use.

Second Embodiment

Figure 2:
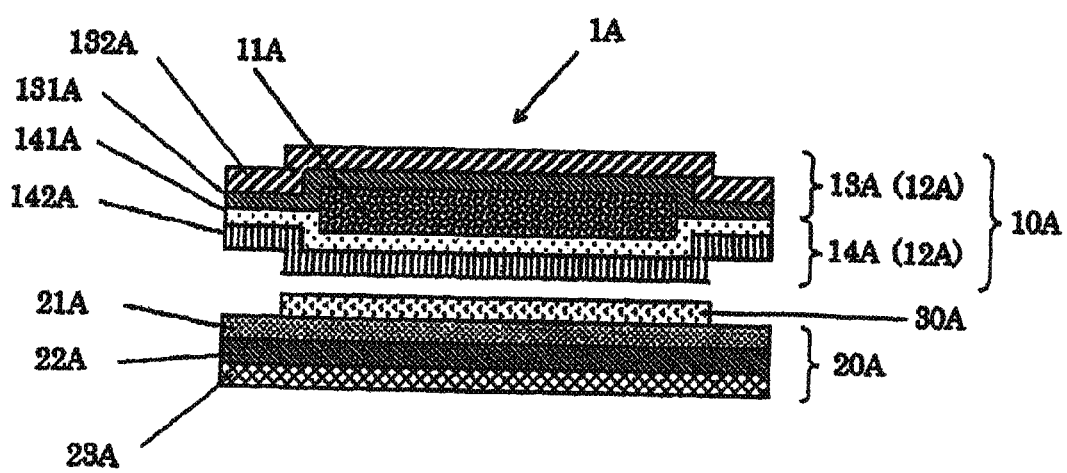
FIG. 2 is a sectional view of a skin patch laminate body, which is Example 2 of the present invention.

FIG. 2 is a sectional view that shows the skin patch laminate body according to the second embodiment. The same explanations for the embodiments described above will not be repeated. It is the same as the embodiment described above in a point that a skin patch laminate body 1A includes a heat imparting body 10A, a skin patch body 20A, and a peelable adhesive layer 30A.

The heat imparting body 10A is formed in a flat shape such that two exothermic agent-accommodating layers 12A accommodate an exothermic agent 11A from the both sides. According to this embodiment, one of the exothermic agent-accommodating layers 12A is a breathable layer 13A for exposing the exothermic agent 11A to air whereby to generate heat oxidatively, and the other exothermic agent-accommodating layer 12A is formed as a non-breathable layer 14A that is not exposed to air. Due to the surface that is attached to the base layer 21A of the skin patch body 20A, which is a non-breathable layer, the surface of the peelable layer in the skin patch body 20A is not necessarily rendered to have air permeability (air path), which makes it possible to enhance adherence of the heat imparting body 10A and the skin patch body 20A.

Similar to the embodiment described above, the breathable layer 13A includes a porous film 131A, which is air-permeable, and a nonwoven cloth 132A. This is because of exposing the exothermic agent 11A to air, and of securing soft touch and feeling when the skin patch laminate body 1A is applied to the skin.

The non-breathable layer 14A that is attached to the base layer 21A of the skin patch body 20A includes a polyethylene film layer (PE layer) 141A and a heat-resistant layer 142A. As a matter of course, the non-breathable layer 14A may be formed only with the PE layer 141A. In addition, the heat-resistant layer 142A is formed of a material having heat-resistance and resilience such as polyethylene terephthalate (PET). As described above, since the heat-resistant layer 142A is provided between the exothermic agent 11A and the peelable adhesive layer 30A, it is possible to reduce the influence of heat emitted from the heat imparting body 10A on the adhesive strength of the peelable adhesive layer 30A. In this embodiment, a polyethylene film is used as a material for the non-breathable layer, and polyethylene terephthalate is used as a material for the heat-resistant layer. However, the material for the non-ventilation layer or for the heat-resistant layer is not limited thereto. In addition, it is possible to use polybutylene terephthalate, nylon or the like as the material for the non-ventilation layer or for the heat-resistant layer.

Similarly to the embodiment described above, the skin patch body 20A has the base layer 21A and the skin adhesive layer 22A on the undersurface of the base layer 21, and further has the release sheet 23A on the undersurface of the skin adhesive layer 22A.

The peelable adhesive layer 30A is located between the base layer 21A of the skin patch body 20A and the non-breathable layer 14A of the heat imparting body 10A, attaches the skin patch body 20A and the heat imparting body 10A, and the heat imparting body 10A, the skin patch body 20A and the peelable adhesive layer 30A are integrated to form the skin patch laminate body 1A.

The skin patch laminate body 1A may be packed in a bag (not shown) that is sealed so that the exothermic agent 11A generates no heat oxidatively. Alternatively, since the non-breathable layer 14A is formed on one of the surfaces, a sheet (not shown) that seals the breathable layer 13A may be set up without packing the skin patch laminate body 1A in a bag so that the exothermic agent 11A is not exposed to oxygen through the breathable layer 13A on the other surface. In any of the cases, in use, the user of the skin patch laminate body 1A takes out the skin patch laminate body 1A packed in a sealed bag from the bag, or peels off the sheet that seals the breathable layer 13A, and the release sheet 23A, and applies the skin patch laminate body 1A to the skin at affected area of the user. Then, when exothermic effects of the heat imparting body 10A disappear, since the heat imparting body 10A and the skin patch body 20A are attached to each other with easy peeling property by the peelable adhesive layer 30A, the user can easily peel off only the heat imparting body 10A retaining the skin patch body 20A as applied to the skin, whereby to retain the skin patch body 20A still having efficacy as applied.

In this embodiment, such peelable agent is first administered to the base layer 21 of the skin patch body 20A, and then is attached to the heat-resistant layer 142A as a non-breathable layer 14A, whereby to form the skin patch laminate body 1A. However, the present invention is not limited thereto.

Figure 3A:
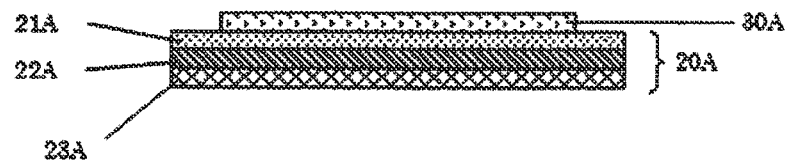
FIG. 3 is view that shows pattern variation of a peelable adhesive layer of the skin patch laminate body, which is Example 2 of the present invention (FIG. 3A is a sectional view of a skin patch body 20A.
FIG. 3B is a pattern of the peelable adhesive layer that is formed on one surface.
FIG. 3C is a pattern of the peelable adhesive layer that is formed as a stripe shape.
FIG. 3D is a pattern of the peelable adhesive layer that is formed as an approximately hexagonal shape).
Figure 3B:
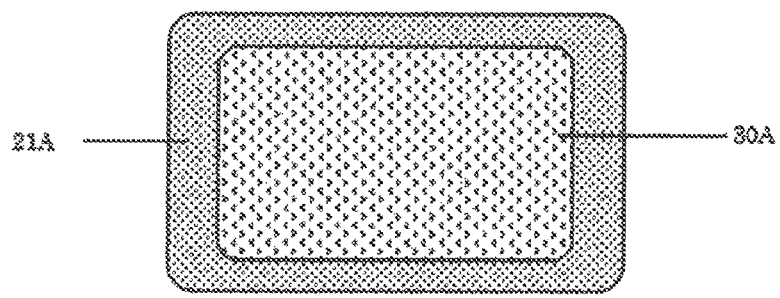
Figure 3C:
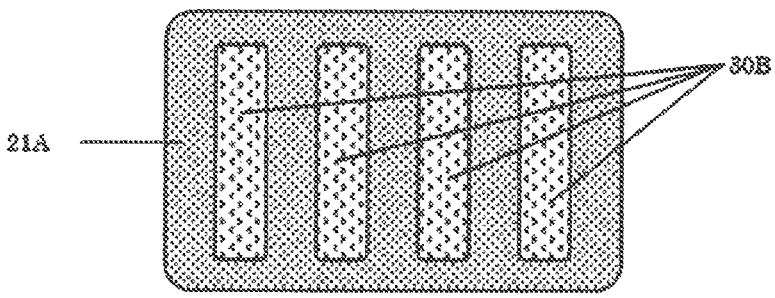

FIGS. 3A to 3D are views that show pattern variation of a peelable adhesive layer in the second embodiment of the skin patch laminate body. FIG. 3A is a sectional view of a skin patch body 20A. FIG. 3B is a pattern of a peelable adhesive layer that is formed on one surface, which corresponds to the sectional view of FIG. 3A. FIG. 3C is a pattern of the peelable adhesive layer 30B that is formed as a stripe shape. It is possible to easily control the adhesive strength by changing the adherend area of the peelable adhesive layer 30B. Specifically, although the same peelable agent is used, the adhesive strength of the peelable adhesive layer 30B can be controlled by partially forming the peelable adhesive layer 30B. For example, the adhesive strength of the peelable adhesive layer 30B can be reduced to a half if the adherend area of the peelable adhesive layer 30B is reduced to a half. Alternatively, when both surfaces of the heat imparting body 10A is rendered to have ventilation, the other surface (the surface of the peelable layer) side may also supply air to the exothermic agent by setting up a peelable adhesive agent layer in a stripe shape as shown in FIG. 3C.

Figure 3D:
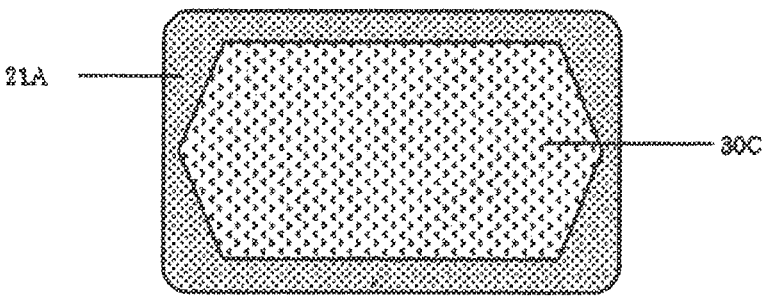

In addition, FIG. 3D is a pattern of a peelable adhesive layer that is formed as an approximately hexagonal shape. It is possible to control the adhesive strength by changing the shape of the peelable adhesive layer 30C. Specifically, for example, when the user rips off the narrow side of the heat imparting body 10A to peel off it in a longitudinal direction, if the peelable adhesive layer has a linear portion to be first peeled off, such as the peelable adhesive layer 30A, peeling off the peelable adhesive layer has trouble. However, if the peelable adhesive layer has a projecting portion such as an apex of a multangular shape, e.g., the peelable adhesive layer 30C, peeling off the peelable adhesive layer becomes easy. In this case, although the adhesive strength of the peelable adhesive layer is elevated to prevent the heat imparting body 10A from being carelessly dropped off, it becomes possible to peel off easily the heat imparting body 10A by the trigger of peeling off.

Although the peelable adhesive layers of a stripe shape and approximately hexagonal shape have been described above, the peelable adhesive layer may have any shape or pattern if the shape or pattern gives control of the adhesive strength or trigger in peeling off the peelable adhesive layer. Such shape or pattern of the peelable adhesive layer 30 may be formed easily by a print type such as gravure print type, offset print type, screen print type and letter press print type using a peelable coating agent as described above. In addition, a mark that indicates a trigger portion of peeling off may be set up on the nonwoven cloth 132A of the heat imparting body 10A to help the user easily find the trigger portion, whereby to easily peel off the heat imparting body 10A.

The shape of the skin patch laminate body in a plan view has been described above as substantially rectangular shape. However, the shape of the skin patch laminate body in a plan view is not limited thereto. The shape of the skin patch laminate body in a plan view may be circular, ellipsoidal, or substantially polygonal shapes. In order to prevent unnecessary peeling off, when the skin patch laminate body has a substantially polygonal shape, it is preferable that the corners are configured to be rounded corners.

What is claimed is:

1. An exothermic skin patch laminate body, comprising:
a skin patch body including a base layer having opposite surfaces and a skin adhesive layer on one of the opposite surfaces of the base layer for being directly applied to the skin; and
a heat imparting body including an exothermic agent and an exothermic agent-accommodating layer that accommodates the exothermic agent therein,
wherein the exothermic agent-accommodating layer of the heat imparting body, and the other of the opposite surfaces of the base layer of the skin patch body are attached to each other via a peelable adhesive layer so that the peelable adhesive layer, the heat imparting body, and the skin patch body are integrated into the exothermic skin patch laminate body with the peelable adhesive layer releasably adhering the heat imparting body and the skin patch body together to allow a user to apply the skin patch body to the skin with the heat imparting body already releasably adhered to the skin patch body without requiring the user to separately apply the heat imparting body onto the skin patch body and to further allow the user to peel off the heat imparting body from the skin patch body after the heat imparting body completes heat generation while the skin patch body remains applied to the skin.

2. The exothermic skin patch laminate body according to claim 1,
wherein the heat imparting body has opposite surfaces, the exothermic agent-accommodating layer comprises first and second exothermic agent-accommodating layers, and the first exothermic agent-accommodating layer includes one of the opposite surfaces of the heat imparting body and is a non-breathable layer, and the second exothermic agent-accommodating layer includes the other of the opposite surfaces of the heat imparting body and is a breathable layer.

3. The exothermic skin patch laminate body according to claim 2,
wherein the exothermic agent-accommodating layer including the one surface of the heat imparting body includes an outer heat-resistant layer.

4. The exothermic skin patch laminate body according to claim 2,
wherein the breathable layer of the heat imparting body includes a porous film and a nonwoven cloth.

5. The exothermic skin patch laminate body according to claim 1,
wherein the heat imparting body has opposite surfaces, the exothermic agent-accommodating layer comprises first and second exothermic agent-accommodating layers, and the first and second exothermic agent-accommodating layers include the respective opposite surfaces of the heat imparting body and are breathable layers.

6. The exothermic skin patch laminate body according to claim 5,
wherein the exothermic agent-accommodating layer including the one surface of the heat imparting body includes an outer heat-resistant layer.

7. The exothermic skin patch laminate body according to claim 3,
wherein the breathable layer of the heat imparting body includes a porous film and a nonwoven cloth.

8. The exothermic skin patch laminate body of claim 5 wherein the peelable adhesive layer has gaps therein for travel of air therethrough and through the breathable exothermic agent-accommodating layer that the peelable adhesive layer releasably adheres to the other surface of the base layer for supplying air to the exothermic agent.

9. The exothermic skin patch laminate body according to claim 1,
wherein the peelable adhesive layer is partially formed between the exothermic agent-accommodating layer of the heat imparting body and the other surface of the base layer of the skin patch body.

10. The exothermic skin patch laminate body according to claim 9,
wherein the peelable adhesive layer is formed with a peelable coating agent.

11. The exothermic skin patch laminate body according to claim 1,
wherein the peelable adhesive layer is formed with a peelable coating agent.

12. The exothermic skin patch laminate body according to claim 1, wherein the skin adhesive layer has opposite surfaces with one of the surfaces on the one surface of the base layer, and further comprising:
a release sheet on the opposite surface, opposing the base layer, of the skin adhesive layer of the skin patch body.

13. The exothermic skin patch laminate body of claim 1 wherein the skin patch body has an outermost perimeter and the heat imparting body has an outermost perimeter with the outermost perimeters of the skin patch body and the heat imparting body being of substantially the same size and configuration such that with the skin patch body and the heat imparting body releasably adhered together no perimeter portions of either one of the bodies projects beyond the other body.

14. The exothermic skin patch laminate body of claim 1 wherein the heat imparting body is entirely above the skin patch body so that only the skin adhesive layer of the skin patch body is used to adhere the exothermic skin patch laminate body to the skin.

15. The exothermic skin patch laminate body of claim 1 wherein the skin patch body and the heat imparting body have substantially identical elongate configurations including opposite longitudinal ends with neither one of the bodies extending beyond the other body, and the peelable adhesive layer is spaced from at least one of the opposite longitudinal ends of each of the bodies that are adjacent to each other to allow for the heat imparting body to be readily peeled off from the skin patch body in a longitudinal direction at the one longitudinal end thereof.

16. The exothermic skin patch laminate body of claim 15 wherein the peelable adhesive layer tapers down to a narrow end portion spaced from the one of the longitudinal ends of each of the bodies that are adjacent to each other.

17. The exothermic skin patch laminate body of claim 1 in combination with a sealed bag wherein both the skin patch body and the heat imparting body releasably adhered together via the peelable adhesive layer to be integrated into the exothermic skin patch laminate body are contained in the sealed bag so that when the sealed bag is opened both the skin patch body and the heat imparting body are simultaneously exposed to air.

18. The exothermic skin patch laminate body of claim 1 wherein the skin adhesive layer includes an adhesive composition and the peelable adhesive layer includes an adhesive agent that has an adhesive strength that is less than that of the adhesive composition of the skin adhesive layer to allow for only the heat imparting body to be peeled off from the skin patch body while the skin patch body remains applied to the skin.

* * * * *